United States Patent [19]

Raghavachari et al.

[11] 4,142,633
[45] Mar. 6, 1979

[54] PACKAGING SYSTEM FOR SYRINGE DISPENSERS

[75] Inventors: Srinivas T. Raghavachari, Chicago; Robert L. Striebel, II, Evanston, both of Ill.

[73] Assignee: MPL, Inc., Chicago, Ill.

[21] Appl. No.: 873,421

[22] Filed: Jan. 30, 1978

Related U.S. Application Data

[63] Continuation-in-part of Ser. No. 713,393, Aug. 11, 1976, abandoned.

[51] Int. Cl.² ............................................. B65D 85/62
[52] U.S. Cl. ..................................... 206/366; 141/27; 206/443; 211/13; 211/72; 422/100
[58] Field of Search .............. 206/366, 365, 364, 443, 206/564, 504, 432, 45.33; 108/43; 220/23.4, 23.83; 23/253 R, 259 R; 294/87.2; 356/246; 211/74, 72, 13; 53/300–390; 141/27, 372, 391

[56] References Cited

U.S. PATENT DOCUMENTS

| | | | |
|---|---|---|---|
| 2,723,484 | 11/1955 | Nelson, Jr. | 220/23.4 |
| 2,990,228 | 6/1961 | Celler | 211/74 |
| 3,078,020 | 2/1963 | Boonstra | 211/74 |
| 3,363,390 | 1/1968 | Crane et al. | 108/43 |
| 3,596,430 | 8/1971 | Parish | 53/390 |
| 3,907,009 | 9/1975 | Dobbins | 141/27 |
| 3,993,452 | 11/1976 | Moulding | 211/74 |
| 4,037,766 | 7/1977 | Iacono | 294/87.26 |

Primary Examiner—William T. Dixson, Jr.
Attorney, Agent, or Firm—Kinzer, Plyer, Dorn & McEachran

[57] ABSTRACT

A packaging arrangement for elongated, flanged syringe dispensers such as hypodermic syringes, oral syringes, and nebulizer injectors of the back-fill type; the dispensers are arranged in a row with the flanges aligned and an elongated plastic connector grips the flanges on each side of the row of dispensers, each connector having a pair of resilient fingers which engage opposite surfaces of the flanges in tightly clamping relationship. The fingers of each connector are formed integrally with a connecting rib, preferably as a plastic extrusion; the tips of the fingers are spaced from each other, before installation on the flanges, a distance less than the thickness of the flanges. The connected row of syringe dispensers is covered by a sealed film to protect them against contamination. The row package may be supported on an open rack for filling dispensers without disturbing the package.

3 Claims, 4 Drawing Figures

U.S. Patent  Mar. 6, 1979  4,142,633
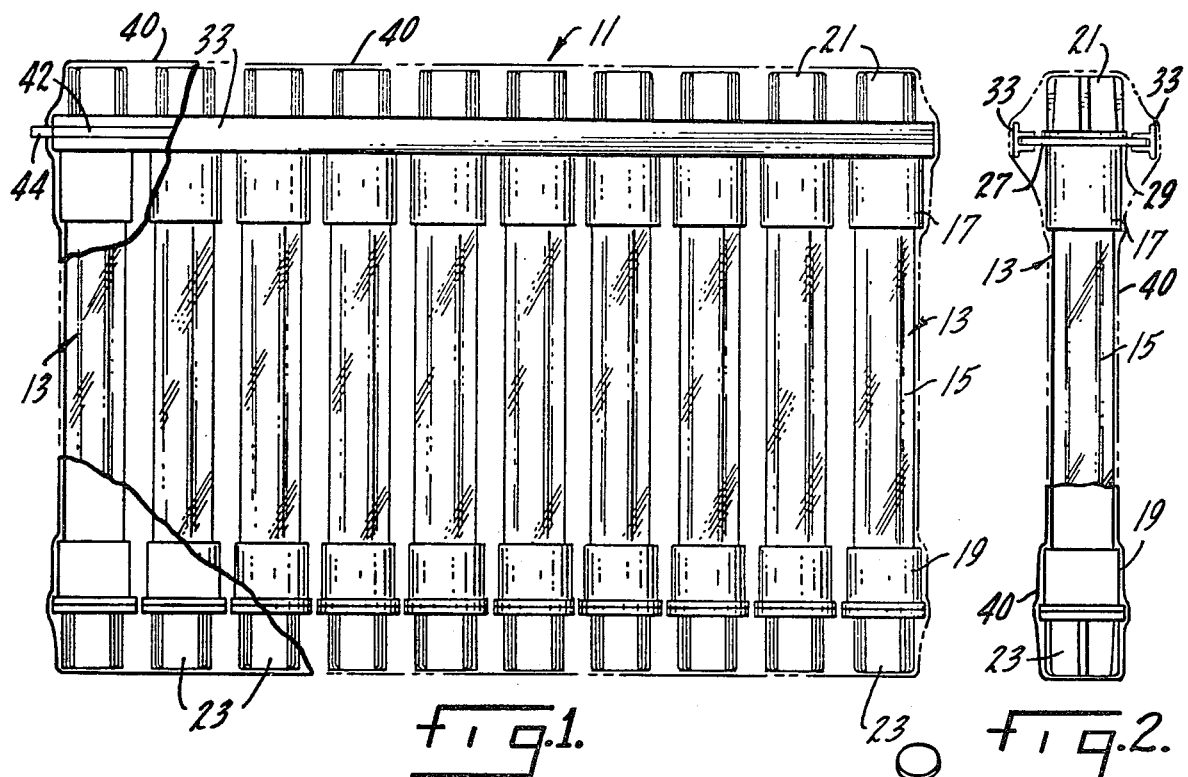
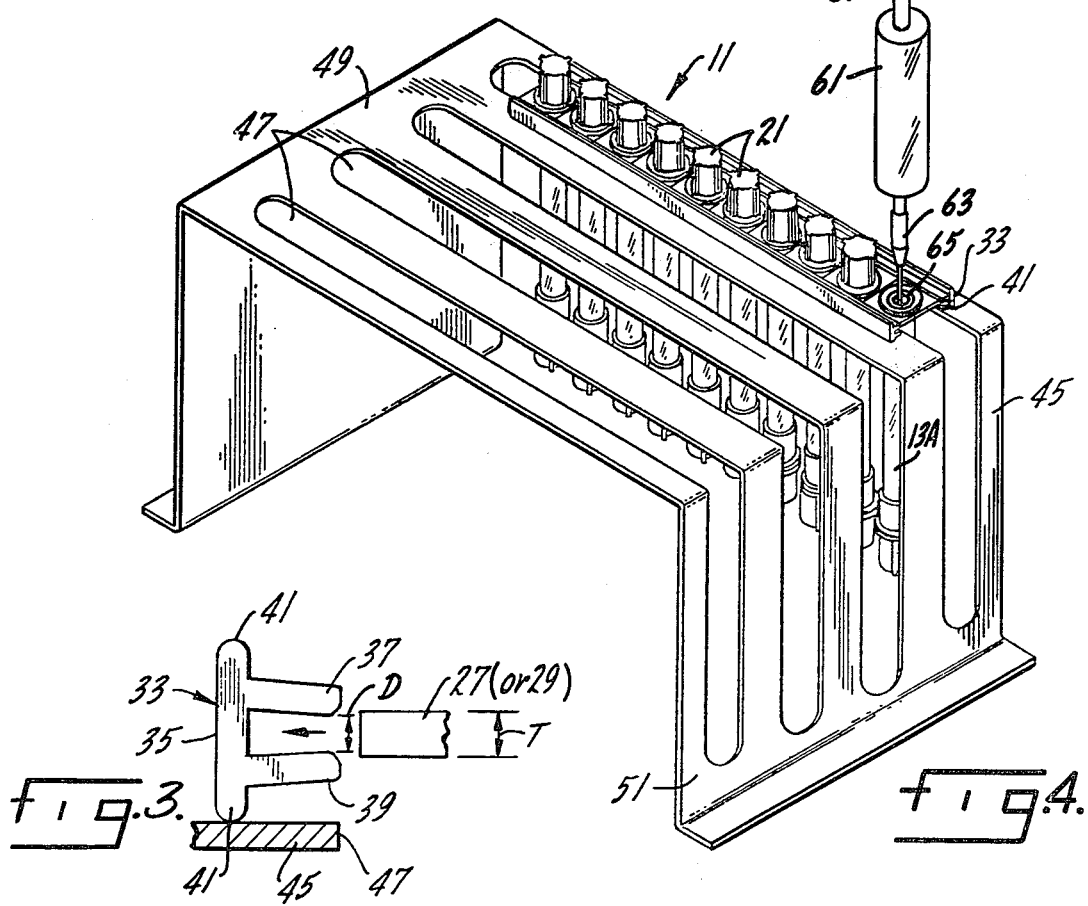

PACKAGING SYSTEM FOR SYRINGE DISPENSERS

CROSS-REFERENCE TO RELATED APPLICATION

This application is a continuation-in-part of U.S. application Ser. No. 713,393 filed Aug. 11, 1976, now abandoned.

BACKGROUND AND SUMMARY OF THE INVENTION

Dispensing devices such as hypodermic syringes, oral syringes, and nebulizer injectors are often intended to be used once and then disposed of. These devices are frequently shipped from the factory or distributor in an unfilled condition; a pharmacist or nurse fills them with the proper dosages of liquid medication to be administered to the patients.

Syringe dispensers are usually shipped to the pharmacist or nurse in packages containing a number of dispensers. These packages may be of any convenient size. For example, a package of twenty hypodermic syringes is commonly used. A typical package includes a vacuum-formed flexible plastic tray enclosed in a heat shrink plastic film. In such a package, the syringes are positioned side by side in cradles which are formed integrally with the plastic tray. When the syringes are of the back-fill type, they are arranged in two banks in the tray with the filling ends of the syringes of each bank facing one another. The tray is grooved or otherwise weakened between the two banks of syringes so that when the heat-shrink plastic film is cut or removed, the tray may be bent along this groove or line of weakness so that the filling ends of the hypodermic syringes are readily accessible for filling. Although this packaging arrangement represents an improvement over previous packages, it is relatively expensive to manufacture and to load with syringes. Additionally, it is somewhat inconvenient to handle during filling. The heat-shrink plastic film is removed to permit bending of the tray but removing the film leaves the syringes free to fall out of the tray as it is stood on end for filling. Also, a separate tray must be provided for each size, type and quantity of dispenser. This causes inventory problems for the manufacturer and limits the packaging arrangements available to the purchaser.

An object of this invention is a simplified packaging arrangement for syringe dispensers, including hypodermic syringes, oral syringes, and nebulizer injectors which reduces the cost of packaging and simplifies filling of the syringe dispensers.

Another object of this invention is a packaging arrangement which permits groups of connected syringe dispensers to be supported on a rack for filling without major alteration of the package.

Another object of this invention is a packaging arrangement which can be used interchangeably with syringe dispensers of various lengths and diameters.

Another object is a packaging arrangement which can easily be adapted to packages containing varying numbers of dispensing units.

Another object is a packaging arrangement which does not cause visual distortion during filling of the individual syringe dispensers.

Another object is a packaging arrangement which requires less storage space for an equal number of syringe dispensers in comparison with conventional packages.

Accordingly, the invention relates to a packaging system for a plurality of syringe dispensers, each dispenser comprising a tubular syringe body having a sealed dispensation orifice at its front end and having a pair of finger-grip flanges projecting radially outwardly from diametrically opposed sides of its back end, each dispenser further including a back end seal through which a medication or the like may be introduced to fill the syringe dispenser. The packaging system comprises a pair of narrow, elongated connectors, each connector including two elongated, resilient opposed fingers having their tip ends spaced by a distance slightly smaller than the thickness of the dispenser flanges, each connector gripping the flanges of an aligned row of syringe dispensers to connect the dispensers together in a compact, coherent row package that can be supported in an open rack to enable filling of the individual dispensers without removing them from the package. A sealed film cover closely encompasses the entire row package to protect the syringe dispensers against contamination.

BRIEF DESCRIPTION OF THE DRAWINGS

The invention is illustrated more or less diagrammatically in the following drawings wherein:

FIG. 1 is a side elevation view of a syringe dispenser package constructed in accordance with the invention, with a part of the package cover cut away to reveal its contents;

FIG. 2 is an end view of the package of FIG. 1, with a part of the cover cut away;

FIG. 3 is an enlarged end view of a connector forming part of the package; and

FIG. 4 is a perspective view of the package of FIG. 1 supported on a filling rack showing one of the syringe dispensers being filled.

DESCRIPTION OF THE PREFERRED EMBODIMENT

FIG. 1 of the drawings shows a package 11 for liquid medication syringe dispensers constructed in accordance with the teachings of this invention. The dispensing devices of this embodiment of the invention are shown as hypodermic syringes 13, but it should be understood that other types of "syringe dispensers," including oral syringes, nebulizer injectors, and the like may be packaged in the same manner. The particular hypodermic syringes 13 shown herein include a tubular glass body 15 having plastic sleeves 17 and 19 fitted onto the glass body at the opposite ends thereof. Friction fit tamperproof caps 21 and 23 are applied respectively over the ends of the sleeves 17 and 19. The lower plastic sleeve 19 forms a dispensation orifice which is constructed to mount a hypodermic needle (not shown). The upper plastic sleeve 17 defines the back end of the dispenser, which is sealed by a rubber plunger in the sleeve. Since the hypodermic syringe depicted is of the back-fill type, the syringes are also filled through the rubber plunger, a slit (not shown) being provided for this purpose. For details of a preferred back-fill syringe construction, which may be used for hypodermic syringes, oral syringes, and nebulizer injectors, reference may be made to U.S. Pat. Nos. 3,729,031 and 3,729,032, issued Apr. 24, 1973 and U.S. Pat. No. 4,048,997 issued Sept. 20, 1977.

Oppositely radially extending flanges 27 and 29, which function as fingergrips, are formed integrally with the plastic sleeve 17 near the outer end of the sleeve. It should be noted that the outer ends of the flanges are arcuate while the sides are flat. This construction of the flanges permits the hypodermic syringes to be positioned close to one another in a row for compactness of packaging.

The hypodermic syringes 13 are held together side by side in a row by a pair of channel-shaped connectors 33. The connectors fit over and engage the flanges 27 and 29 respectively located on the opposite sides of the row of dispensing devices. The connectors are preferably extruded from a relatively stiff but somewhat resilient plastic. A suitable plastic is a low density polyethylene, but it should be understood that other suitable plastics may also be used. Nor should the invention be limited to connectors which are formed by extrusion, since suitable connectors may be formed in any one of the customary plastic molding and forming techniques.

Each connector 33 includes a backbone or base 35 from which extend a pair of spaced resilient fingers 37 and 39 (FIG. 3). The fingers are inclined somewhat towards each other but may terminate short of contacting each other. In order to provide the fingers with a clamping action, the distance D between the tips of the fingers is constructed so that it is less than the thickness T of the flanges 27 and 29 of the syringes. The dimensions of the fingers 37, 39 and the backbone 35 forming the connector may vary, but the connector should be sufficiently strong to support the syringe dispensers held thereby when the dispensers are filled with liquid medication.

The packaging arrangement also includes a sealed film cover 40. This cover can be a heat-shrink plastic film or any other suitable covering material, preferably transparent. The purpose of the cover 40 is to provide an additional barrier to contamination of the syringe. Thus, the cover 40 encompasses the entire package (FIGS. 1 and 2). An opening tape 42 preferably extends around the top of the package 11; the tape may include a pull-tab 44. Pulling the tab 44 causes the opening tape 42 to sever the top portion of the film cover from the bottom portion, permitting easy removal of at least the top portion of the cover when the syringes 13 are ready for filling. Tape opening arrangements of this type being common in various packaging systems (e.g., cigarettes), no further description is deemed necessary.

The backbone 35 of the connector 33 extends beyond the fingers 37 and 39 to provide ribs 41, one of which engages a supporting surface when a row package 11 is placed on a rack 45, as shown in FIGS. 3 and 4. The rack 45 (FIG. 4) has continuous slots 47 formed in the top and end walls 49 and 51 so that packages 11 of syringe dispensers can be inserted into the slots from above or through the end wall, and are supported on the top wall. The package rests on the connector ribs when in the rack. The packaging arrangement of this invention permits a package of dispensing devices to be inserted into the rack without requiring removal of the connectors 33. Dispensing devices of the back-fill type can be filled in the rack while held together by the connectors. Thus, the filling and handling of the dispensing devices is greatly facilitated, and the narrow connectors 33 add little or no bulk to the total package.

The back-filling operation is shown in FIG. 4. The syringe 13A being filled has its cap 21 removed. A fill cylinder 61 containing a supply of medication is connected into the back end of the syringe 13A by means of a fill needle 63. The fill needle protrudes through a slitted opening in a rubber plunger 65. The plunger 65 fits snugly in the back end of the syringe (the upper end as seen in FIG. 4), and normally affords a back end seal for the syringe. A piston and rod assembly 67 in the fill cylinder 61 is used to inject the medication into the syringe 13 through the fill needle 63. Each of the syringes in the row package is filled in the same manner. When a syringe is ready for use, it is pulled from between the connectors and fitted with a plunger rod at the back end and a needle at the front end. This method of packaging and handling syringe dispensers greatly reduces the chance of contamination because the syringes are handled individually only once, immediately prior to use.

We claim:

1. A packaging system for a plurality of syringe dispensers, each dispenser comprising a tubular syringe body having a sealed dispensation orifice at its front end and having a pair of finger-grip flanges projecting radially outwardly from diametrically opposed sides of its back end, each dispenser further including a back end seal through which a medication or the like may be introduced to fill the syringe dispenser, the packaged system comprising:

a pair of narrow, elongated connectors, each connector including two elongated, resilient opposed fingers having their tip ends spaced by a distance slightly smaller than the thickness of the dispenser flanges, each connector gripping the flanges of an aligned row of syringe dispensers to connect the dispensers together in a compact, coherent row package that can be supported in an open rack to enable filling of the individual dispensers without removing them from the package;

and a sealed film cover closely encompassing the entire row package to protect the syringe dispensers against contamination.

2. The syringe dispenser packaging system of claim 1 in which each connector is formed as a unitary integral plastic extrusion.

3. The syringe dispenser packaging system of claim 1, the system further comprising a rack having a horizontal top support plate with at least one elongated slot therein wide enough to pass the tubular syringe bodies but narrower than the span of the syringe flanges, for supporting the row package with the back ends of the syringe dispensers exposed for filling while still in the package.

* * * * *